United States Patent
Brinza et al.

(10) Patent No.: US 9,957,551 B2
(45) Date of Patent: May 1, 2018

(54) SYSTEMS AND METHODS FOR VALIDATION OF SEQUENCING RESULTS

(71) Applicant: LIFE TECHNOLOGIES CORPORATION, Carlsbad, CA (US)

(72) Inventors: Dumitru Brinza, Montara, CA (US); Fiona Hyland, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 331 days.

(21) Appl. No.: 14/711,501

(22) Filed: May 13, 2015

(65) Prior Publication Data
US 2015/0329899 A1 Nov. 19, 2015

Related U.S. Application Data

(60) Provisional application No. 61/992,306, filed on May 13, 2014.

(51) Int. Cl.
*C12Q 1/68* (2006.01)
*G06F 19/22* (2011.01)

(52) U.S. Cl.
CPC ......... *C12Q 1/6806* (2013.01); *C12Q 1/6858* (2013.01); *C12Q 1/6869* (2013.01); *G06F 19/22* (2013.01)

(58) Field of Classification Search
None
See application file for complete search history.

(56) References Cited

U.S. PATENT DOCUMENTS

| | | |
|---|---|---|
| 2009/0026082 A1 | 1/2009 | Rothberg et al. |
| 2009/0127589 A1 | 5/2009 | Rothberg |
| 2009/0325145 A1 | 12/2009 | Sablon et al. |
| 2010/0137143 A1 | 6/2010 | Rothberg et al. |
| 2010/0197507 A1 | 8/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2012/0295819 A1 | 11/2012 | Leamon et al. |
| 2013/0345066 A1 | 12/2013 | Brinza et al. |

FOREIGN PATENT DOCUMENTS

| | | |
|---|---|---|
| WO | 2006/084131 | 8/2006 |
| WO | 2012/044847 | 4/2012 |
| WO | 2013/068528 | 5/2013 |

OTHER PUBLICATIONS

Albers, C. A. et al., "Dindel: Accurate Indel Calls from Short-Read Data", *Genome Research*, vol. 21, 2011, 961-973.
(Continued)

*Primary Examiner* — Samuel C Woolwine

(57) ABSTRACT

Systems and method for validation of sequencing results can amplify a target region of a nucleic acid sample in the presence of a primer pool including target specific and variant specific primers. The variant specific primers can include variant specific barcodes and variant specific sequences. An amplicon can be sequenced to determine the sequence of the variant specific barcode. The variant can be identified based on the sequence of the variant specific barcode, and the location of the variant can be determined by mapping the amplicon to a reference sequence.

16 Claims, 6 Drawing Sheets

1K hp specific primers = 100% hp accuracy

- Ion homopolymer error rate is high for hp longer than 6.
- In Ion AmpliSeq panels hp longer than 6 are the major cause of FP and FN.
- Here we propose to design a set of hp-specific primers that can be used in combination with any custom design primers, and help unambiguously determine the length of long hp regions.
- hp-specific primers can be made just once, and then used in multiple experiments.
- The body of hp-specific primer has 4 components, example of one of the primers that targets A 6-mer

- Protocol
  - (1) PCR with custom design primers (1.1) Apply Uracil cleavage (optional)
  - (2) extract half of amplified in (1) sample and PCR it with custom design and hp-specific primers (possible change to PCR conditions)
- Product

- Readings started at hp-specific primers will have the length of homopolymer encoded in the barcoded part of the primer
- Portion of hp-specific reads can be reduced from 20% to 5% depending on overall coverage

(56) References Cited

OTHER PUBLICATIONS

De Leeneer, K. et al., "Massive Parallel Amplicon Sequencing of the Breast Cancer Genes BRCA1 and BRCA2: Opportunities, Challenges, and Limitations", *Human Mutuation,* vol. 32, No. 3, Feb. 8, 2011, 335-344.
Linnertz, C. et al., "Characterization of the Poly-T Variant in the TOMM40 Gene in Diverse Populations", *PLoS One,* vol. 7, No. 2, Feb. 6, 2012, 1-5.
PCT/US2015/030615, International Search Report and Written Opinion dated Aug. 14, 2015, 11 Pages.
Ruiz, A. et al., "Genetic Testing in Hereditary Breast and Ovarian Cancer Using Massive Parallel Sequencing", *BioMed Research International,* vol. 2014, Jun. 26, 2014, 1-8.
Sambrook, J. et al., "Molecular Cloning: A Laboratory Manual", Third ed., *Cold Spring Harbor Laboratory Press,* Cold Spring Harbor, N.Y., 2000.

SYSTEMS AND METHODS FOR VALIDATION OF SEQUENCING RESULTS

CROSS-REFERENCE TO RELATED APPLICATIONS

This application claims the benefit of priority under 35 U.S.C. § 119 to U.S. Provisional Application No. 61/992,306, filed May 13, 2014, the disclosures of which is incorporated herein by reference in its entirety.

SEQUENCE LISTING

The instant application contains a Sequence Listing which has been sebmitted electronically in ASCII format and is hereby incorporated bu reference in its entirety. Said ASCII copy, created on Aug. 17, 2017, is named LT00766_SL.txt and is 968 bytes in size.

Throughout this application various publications, patents, and/or patent applications are referenced. The disclosures of these publications, patents, and/or patent applications in their entireties are hereby incorporated by reference into this application in order to more fully describe the state of the art to which this invention pertains.

FIELD

The present disclosure generally relates to the field of nucleic acid sequencing including systems and methods for validation of sequencing results.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible. These goals can be reached through the use of sequencing platforms and methods that provide sample preparation for samples of significant complexity, sequencing larger numbers of samples in parallel (for example through use of barcodes and multiplex analysis), and/or processing high volumes of information efficiently and completing the analysis in a timely manner. Various methods, such as, for example, sequencing by synthesis, sequencing by hybridization, and sequencing by ligation are evolving to meet these challenges.

Ultra-high throughput nucleic acid sequencing systems incorporating NGS technologies typically produce a large number of short sequence reads. Sequence processing methods should desirably assemble and/or map a large number of reads quickly and efficiently, such as to minimize use of computational resources. For example, data arising from sequencing of a mammalian genome can result in tens or hundreds of millions of reads that typically need to be assembled before they can be further analyzed to determine their biological, diagnostic and/or therapeutic relevance.

Exemplary applications of NGS technologies include, but are not limited to: genomic variant detection, such as insertions/deletions, copy number variations, single nucleotide polymorphisms, etc., genomic resequencing, gene expression analysis and genomic profiling.

From the foregoing it will be appreciated that a need exists for systems and methods that can validate sequencing results.

DRAWINGS

For a more complete understanding of the principles disclosed herein, and the advantages thereof, reference is now made to the following descriptions taken in conjunction with the accompanying drawings, in which:

FIG. 6 discloses SEQ ID NOS 1-3, respectively, in order of appearance.

Figure 1:
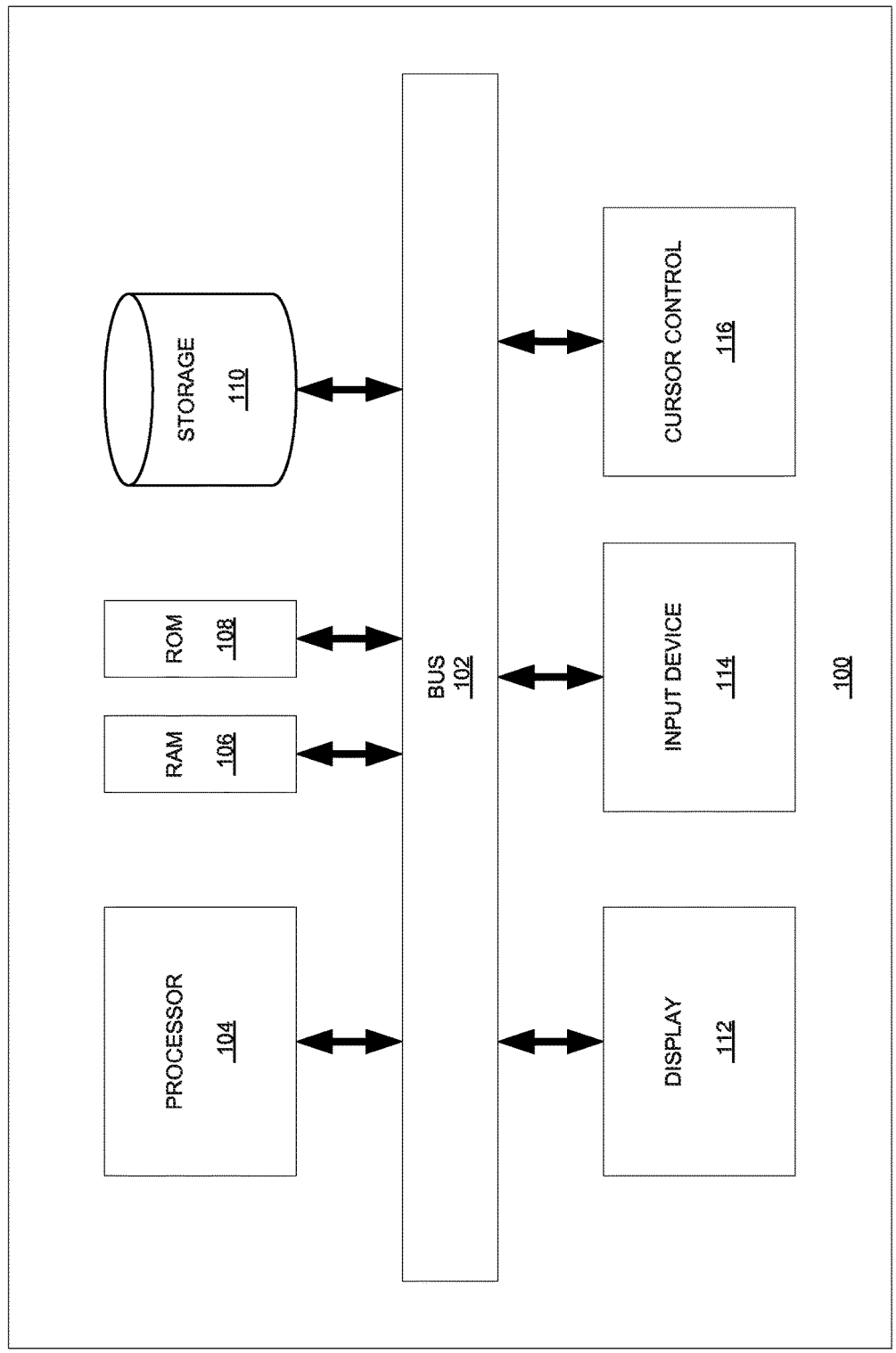
FIG. 1 is a block diagram that illustrates an exemplary computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for detecting low frequency variants are described herein, which includes the accompanying Figures.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, number of bases, coverage, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well-known and commonly used in the art.

In various embodiments, a "system" sets forth a set of components, real or abstract, comprising a whole where each component interacts with or is related to at least one other component within the whole.

In various embodiments, a "biomolecule" may refer to any molecule that is produced by a biological organism, including large polymeric molecules such as proteins, polysaccharides, lipids, and nucleic acids (DNA and RNA) as well as small molecules such as primary metabolites, secondary metabolites, and other natural products.

In various embodiments, the phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the Personal Genome Machine (PGM) and Proton of Life Technologies Corp. provide massively parallel sequencing with enhanced accuracy. The PGM and Proton Systems and associated workflows, protocols, chemistries, etc. are described in more detail in U.S. Patent Application Publication No. 2009/0127589 and No. 2009/0026082, the entirety of each of these applications being incorporated herein by reference.

In various embodiments, the phrase "sequencing run" refers to any step or portion of a sequencing experiment performed to determine some information relating to at least one biomolecule (e.g., nucleic acid molecule).

In various embodiments, the phase "base space" refers to a representation of the sequence of nucleotides. The phase "flow space" refers to a representation of the incorporation event or non-incorporation event for a particular nucleotide flow. For example, flow space can be a series of values representing a nucleotide incorporation event (such as a one, "1") or a non-incorporation event (such as a zero, "0") for that particular nucleotide flow. Nucleotide flows having a non-incorporation event can be referred to as empty flows, and nucleotide flows having a nucleotide incorporation event can be referred to as positive flows. It should be understood that zeros and ones are convenient representations of a non-incorporation event and a nucleotide incorporation event; however, any other symbol or designation could be used alternatively to represent and/or identify these events and non-events. In particular, when multiple nucleotides are incorporated at a given position, such as for a homopolymer stretch, the value can be proportional to the number of nucleotide incorporation events and thus the length of the homopolymer stretch.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems (such as Illumina HiSeq, MiSeq, and Genome Analyzer), hybridization-based systems, direct or indirect nucleotide identification systems, pyrosequencing (such as 454 Life Science GS FLX and GS Junior), ion- or pH-based detection systems (such as Ion Torrent), electronic signature-based systems (such as Oxford Nanopore GridION and MinION), etc.

In various embodiments, a "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

In various embodiments, a "structural variant" refers to a variation in the structure of a chromosome. Structural variants can include deletions, duplications, copy-number variants, insertions, gene fusions, inversions and translocations. Many of structural variants are associated with genetic diseases, however more are not.

Multiplex Amplification Methods:

In various embodiments, target nucleic acids generated by the amplification of multiple target-specific sequences from a population of nucleic acid molecules can be sequenced. In some embodiments, the amplification can include hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences. In some embodiments, the amplified target sequences can be ligated to one or more adaptors. In some embodiments, the adaptors can include one or more nucleotide barcodes or tagging sequences. In some embodiments, the amplified target sequences once ligated to an adaptor can undergo a nick translation reaction and/or further amplification to generate a library of adaptor-ligated amplified target sequences. Exemplary methods of multiplex amplification are described in U.S. application Ser. No. 13/458,739 filed Nov. 12, 2012 and titled "Methods and Compositions for Multiplex PCR."

In various embodiments, the method of performing multiplex PCR amplification includes contacting a plurality of target-specific primer pairs having a forward and reverse primer, with a population of target sequences to form a plurality of template/primer duplexes; adding a DNA polymerase and a mixture of dNTPs to the plurality of template/primer duplexes for sufficient time and at sufficient temperature to extend either (or both) the forward or reverse primer in each target-specific primer pair via template-dependent synthesis thereby generating a plurality of extended primer product/template duplexes; denaturing the extended primer product/template duplexes; annealing to the extended primer product the complementary primer from the target-specific primer pair; and extending the annealed primer in the presence of a DNA polymerase and dNTPs to form a plurality of target-specific double-stranded nucleic acid molecules.

Adaptor-Joining Methods:

In some embodiments, the present teachings are directed to methods for preparing a library of polynucleotide constructs which can include an adaptor-joining step. In some embodiments, a plurality of polynucleotide fragments can include at least two polynucleotide fragments that are joined to one or more nucleic acid adaptors by hybridization (e.g., with or without a primer extension reaction) or enzymatic ligation (e.g., a ligase reaction) to generate adaptor-fragment constructs. In some embodiments, one end or both ends of polynucleotide fragments can be joined to at least one type of adaptor. One or both ends of a polynucleotide fragment can be joined to at least one nucleic acid adaptor, including barcoded adaptors, sequencing primer adaptors, amplification primer adaptors, universal adaptors, blocking oligonucleotide adaptors and/or others.

In some embodiments, an adaptor can include nucleotide sequences that are complementary to sequencing primers (e.g., P1, P2 and/or A), amplification primers, universal sequences and/or barcode sequences. For example, released mate pair constructs can be joined at each end to a different sequencing adaptor to prepare a nucleic acid library for sequencing with SOLiD™ sequencing reactions (WO 2006/084131) or sequencing with ion-sensitive sequencing reactions (e.g., Ion Torrent PGM™ and Proton™ sequencers from Life Technologies Corporation, see for example U.S. Patent Publication Nos. 2010/0301398, 2010/0300895, 2010/0300559, 2010/0197507, 2010/0137143, 2009/0127589; and 2009/0026082, which are incorporated by reference in their entireties).

Barcoded Adaptor Sequences

In some embodiments, the present teachings are directed to methods for preparing a library of polynucleotide constructs which can include joining at least one end of a plurality of polynucleotide fragments to an adaptor having a barcode sequence. A barcode sequence can be a selected sequence of nucleotide bases (e.g. adenine, guanine, cytosine, thymine, uracil, inosine, or analogs thereof) in the polynucleotide strand that serves to identify the polynucleotide strand and/or distinguish it from other polynucleotide strands (e.g. those containing a different target sequence of interest). In some embodiments, a barcode adaptor can include a unique identification sequence (e.g., barcode sequence). A barcode sequence can be used for various purposes, such as tracking, sorting, and/or identifying the samples.

Because different barcode sequences can be associated with different polynucleotide strands, these barcode sequences may be useful in multiplexed sequencing of different samples. In some embodiments, a barcode adaptor can be used for constructing multiplex nucleic acid libraries. In some embodiments, one or more barcode sequences can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences. Examples of various adaptors having barcode sequences can be found in PCT/US2011/054053 which is incorporated by reference in its entirety.

In various high throughput DNA sequencing technologies (such as sequencing-by-synthesis) it is desirable to permit sequencing of different samples that are pooled together for simultaneous analysis (sometimes referred to as multiplexed sequencing).

When carrying out multiplexed sequencing, it is generally desirable to identify the origin of each sample, and this may require that the sequencing data be deconvolved for each sample. In particular, it can be desirable to uniquely identify the source of the sequence data derived from a multiplex sample (for example, to identify a particular nucleic acid species associated with different sample populations). One approach to facilitate sample identification is the use of unique nucleic acid identifier sequences (barcode adaptors) that are embedded within the sample construct so that sequencing data can be correctly identified or associated with its source sample.

Computer-Implemented System

FIG. 1 is a block diagram that illustrates an exemplary computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

In various embodiments, the term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Nucleic Acid Sequencing Platforms

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 2:
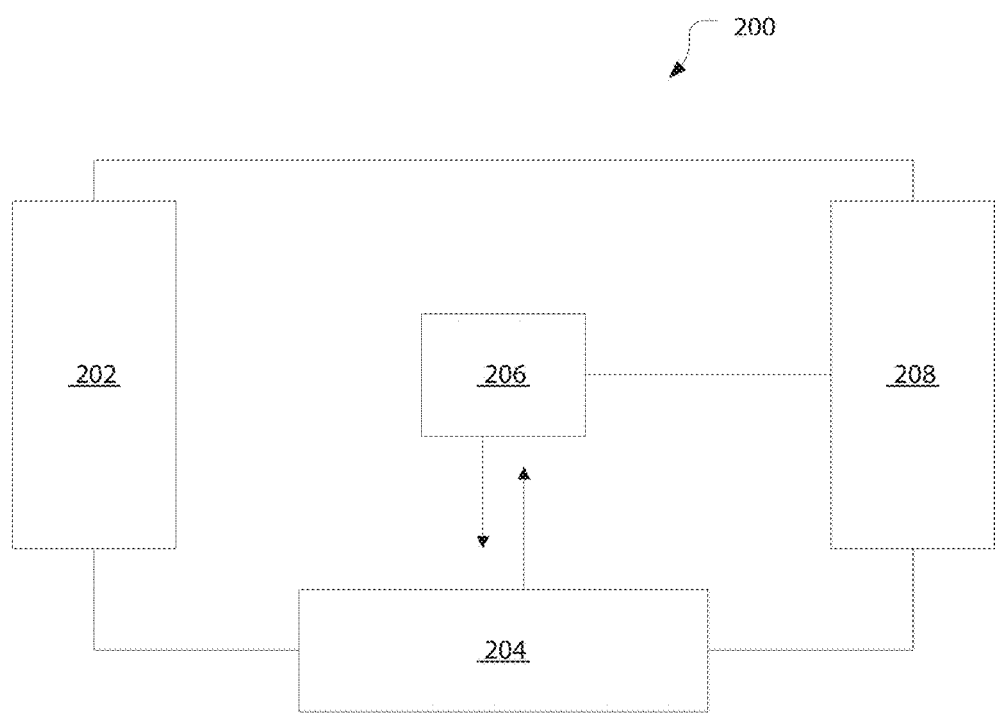
FIG. 2 is a schematic diagram of an exemplary system for reconstructing a nucleic acid sequence, in accordance with various embodiments.

Various embodiments of nucleic acid sequencing platforms, such as a nucleic acid sequencer, can include components as displayed in the block diagram of FIG. 2. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082 are incorporated herein by reference. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145, the entirety of which being incorporated herein by reference) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

System and Methods for Identifying Sequence Variation

Figure 3:
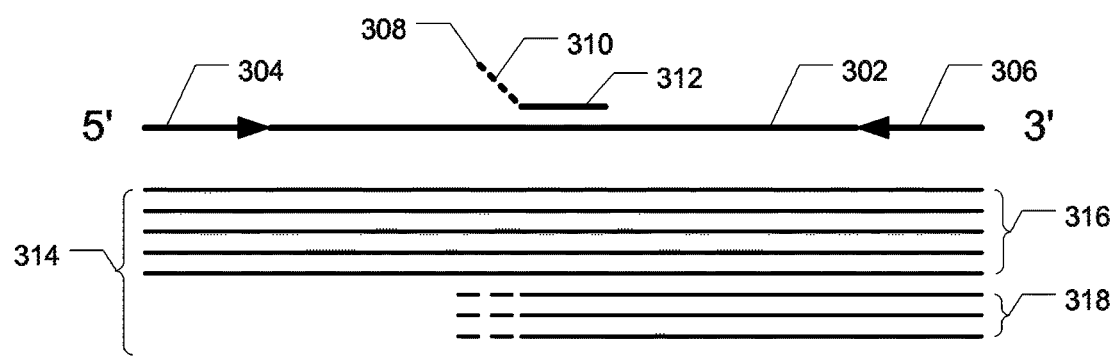
FIG. 3 is a schematic diagram of illustrating amplification products, in accordance with various embodiments.

FIG. 3 is a diagram showing exemplary amplification products. Target region 302 can be amplified using target specific primer 304, target specific primer 306 and variant specific primer 308. Variant specific primer 308 can include a variant specific barcode region 310 and a variant sequence region 312. Amplification of the target region can produce amplicons 314. Specifically, amplification by target specific primers 304 and 306 can produce full length target amplicons 316 while amplification by variant specific primer 308 and target specific primer 306 can produce variant specific amplicons 318.

Figure 6:
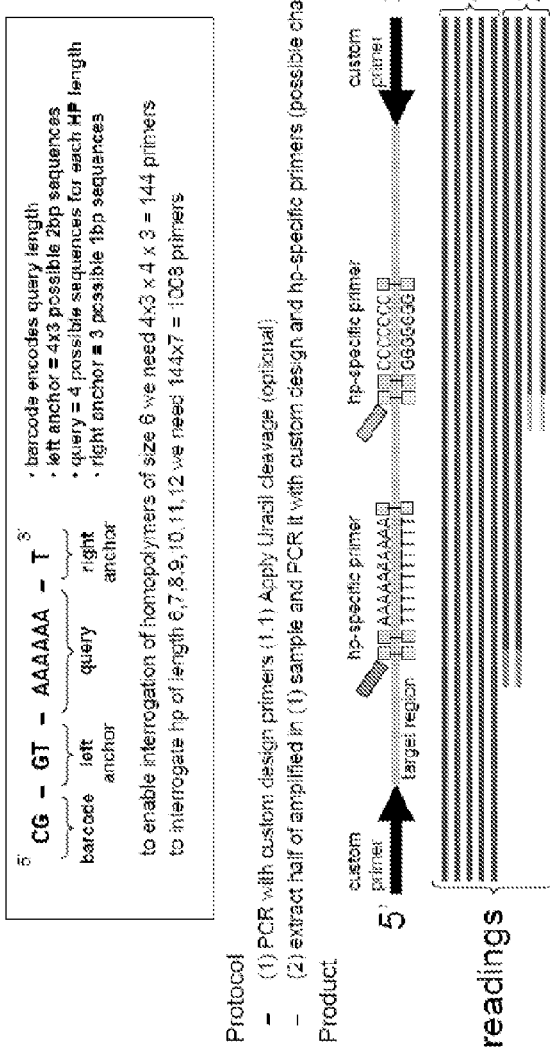
FIG. 6 is a summary and a schematic diagram illustrating an exemplary method of validating homopolymer sequencing results, in accordance with various embodiments.

In various embodiments, a primer pool using a plurality of variant specific primers could be used. For example, to verify the length of a homopolymer region, variant specific primers having multiple lengths of homopolymers could be used, with different variant specific barcode region corresponding to each different length. An exemplary variant specific primer for verifying a homopolymer region is shown in FIG. 6 and described in further detail herein.

By way of another example, to verify a SNP, variant specific primers corresponding to reference sequence and the SNP could be used. Additional sequence specific primers corresponding to the other alternative bases at the position could also be used.

In various embodiments, the sequence differences between the variant specific barcodes can provide a greater differentiation in the raw data from the sequencing instrument than for the variant, such that the distinguishing power is greater for the barcode than for the variant. For example, a change in the length of a homopolymer may produce only a small change in the raw data that may be the result of a sequencing error, but a change of multiple bases in the barcode could produce a change in the raw data that would require multiple sequencing errors to occur in a specific order to happen by chance.

In various embodiments, full length target amplicons can be produced by amplifying the target sequence in a first PCR reaction without the variant specific primers and variant specific amplicons can be produced by amplifying the target sequence, or the full length amplicons, in a second PCR reaction with the variant specific primers. Alternatively, full length target amplicons and variant specific amplicons can be produced substantially simultaneously by performing a multiplex PCR reaction with both the target specific primers and the variant specific primers present. A large excess of target specific primers, relative to the variant specific primers, may be used to ensure a sufficient quantity of full length target amplicons is produced.

FIG. 6 shows a summary and schematic diagram illustrating a method for identifying or verifying homopolymer variants, in accordance with various embodiments.

The accurate sequencing of homopolymer regions can pose difficulties in sequencing systems, particularly when sequencing longer homopolymer stretches, such as those around or longer than hexa-(6)-mers. As a result, sequencing systems can yield false positives (FP), or false negatives (FN) when identifying or verifying a homopolymer region.

In various embodiments, as exemplified in FIG. 6, a set of homopolymer-specific variant primers can be used to identify and/or verify a homopolymer region. In various embodiments, the variant primers include, without limitation, a barcode region, a left (upstream) anchor region, a query (e.g., homopolymer) region, and a right (downstream) anchor region. In the example depicted, the barcode is formed by two (2) base-pairs, the left anchor is formed by two (2) base-pairs, the query region is formed from (5) base pairs, and the right anchor is formed by one (1) base-pair. Other sequence lengths and compositions are envisioned in various embodiments, and the length or sequence of any given region in the variant specific primer are not necessarily correlated to or dependent on the length or sequence of any other region. In various embodiments, the length or sequence of the barcode region in a given variant specific primer is correlated to or dependent on the length or sequence of one or more given query regions.

In various embodiments, a set of variant specific primers includes multiple permutations of the various regions. For example, as shown in FIG. 6, a set of variant specific primers of the type depicted would include a specific barcode sequence that is indicative of a specific homopolymer length. In this example, the barcode sequence of "CG" corresponds to the set of variant specific primers that would verify or identify a hexameric homopolymer region of any of the four natural bases. Thus, for such a set, the set of variant specific primers would include (a) all possible dinucleotide left anchor sequences that do not contain a second base that matches the downstream query sequence homopolymer (i.e., 12 possible sequences), (b) all possible homo-hexameric sequences in the query region (i.e., 4 possible sequences: hexa-A, hexa-G, hexa-T and hexa-C), (c) all possible mononucleotide right anchor sequences that do not contain a base that matches the upstream query sequence homopolymer (i.e., 3 possible sequences), thereby giving a total of 144 possible primers for this exemplary set.

In various embodiments, to form a variant specific primer set that can identify or verify any homopolymer ranging from 6 to 12-mer, a set of 144 permutations can generated in an analogous manner.

In various embodiments, the barcode region can be lengthened to allow for a larger number of query sequences to be verified or identified. In various embodiments, the barcode can be varied such that homopolymers of differing sequences can be identified with different barcodes.

As schematically depicted in FIG. 6 and described herein, the variant specific primers can be amplified, either concurrently or sequentially, with each other and one or more target specific primers. In this manner, the variant specific primers will, in conjunction with an opposing target specific primer, generate a set of amplicons that correspond to the homopolymer region. In this manner, sequencing of the set of amplicons generated will result in an identification of a barcode sequence in conjunction with its corresponding homopolymer query region.

Figure 4:
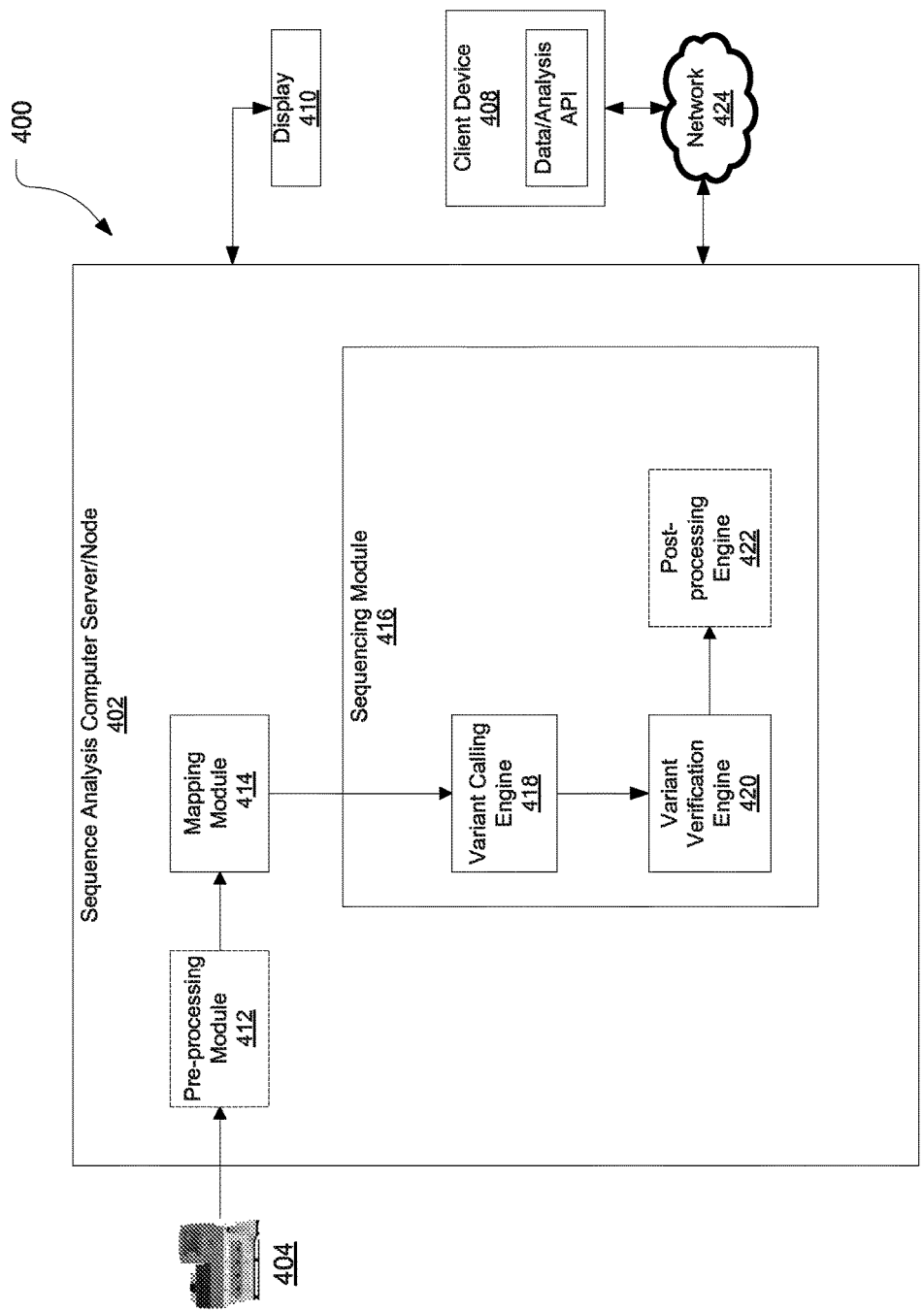
FIG. 4 is a schematic diagram of an exemplary genetic analysis system, in accordance with various embodiments.

FIG. 4 is a schematic diagram of a system for identifying variants, in accordance with various embodiments.

As depicted herein, variant analysis system 400 can include a nucleic acid sequence analysis device 404 (e.g., nucleic acid sequencer, real-time/digital/quantitative PCR instrument, microarray scanner, etc.), an analytics computing server/node/device 402, and a display 410 and/or a client device terminal 408.

In various embodiments, the analytics computing sever/node/device 402 can be communicatively connected to the nucleic acid sequence analysis device 404, and client device terminal 408 via a network connection 424 that can be either a "hardwired" physical network connection (e.g., Internet, LAN, WAN, VPN, etc.) or a wireless network connection (e.g., Wi-Fi, WLAN, etc.).

In various embodiments, the analytics computing device/server/node 402 can be a workstation, mainframe computer, distributed computing node (such as, part of a "cloud computing" or distributed networking system), personal computer, mobile device, etc. In various embodiments, the nucleic acid sequence analysis device 404 can be a nucleic acid sequencer, real-time/digital/quantitative PCR instrument, microarray scanner, etc. It should be understood, however, that the nucleic acid sequence analysis device 404 can essentially be any type of instrument that can generate nucleic acid sequence data from samples obtained from an individual.

The analytics computing server/node/device 402 can be configured to host an optional pre-processing module 412, a mapping module 414, and a sequencing module 416.

Pre-processing module 412 can be configured to receive from the nucleic acid sequence analysis device 404 and perform processing steps, such as conversion from f space to base space, color space to base space, or from flow space to base space, determining call quality values, preparing the read data for use by the mapping module 414, and the like.

The mapping module 414 can be configured to align (i.e., map) a nucleic acid sequence read to a reference sequence. Generally, the length of the sequence read is substantially less than the length of the reference sequence. In reference sequence mapping/alignment, sequence reads are assembled against an existing backbone sequence (e.g., reference sequence, etc.) to build a sequence that is similar but not necessarily identical to the backbone sequence. Once a backbone sequence is found for an organism, comparative sequencing or re-sequencing can be used to characterize the genetic diversity within the organism's species or between closely related species. In various embodiments, the reference sequence can be a whole/partial genome, whole/partial exome, etc.

In various embodiments, the sequence read and reference sequence can be represented as a sequence of nucleotide base symbols in base space. In various embodiments, the sequence read and reference sequence can be represented as one or more colors in color space. In various embodiments, the sequence read and reference sequence can be represented as nucleotide base symbols with signal or numerical quantitation components in flow space.

In various embodiments, the alignment of the sequence fragment and reference sequence can include a limited number of mismatches between the bases that comprise the sequence fragment and the bases that comprise the reference sequence. Generally, the sequence fragment can be aligned to a portion of the reference sequence in order to minimize the number of mismatches between the sequence fragment and the reference sequence.

The sequencing module 416 can include a variant calling engine 418, a variant verification engine 420, and an optional post processing engine 422. In various embodiments, sequencing module 416 can be in communications with the mapping module 414. That is, sequencing module 416 can request and receive data and information (through, e.g., data streams, data files, text files, etc.) from mapping module 414.

The variant calling engine 418 can be configured to receive mapped reads from the mapping module 414, and identify differences between the aligned reads and the reference sequence. Exemplary methods of identifying variations are described in U.S. application Ser. No. 13/890,923, filed May 9, 2013 and titled "SYSTEMS AND METHODS FOR IDENTIFYING SEQUENCE VARIATION".

Variant verification engine 420 can be configured to receive mapped reads from the mapping module 414. The variant verification engine 420 can identify the variant specific barcodes associated with variant specific reads mapped to candidate variant locations. The variant verification engine 420 can use the barcodes to verify candidate variants identified by the variant calling engine 418.

Post processing engine 422 can be configured to receive the variants identified by the variant calling engine 418 and the variant verification engine 420 and perform additional processing steps, such as filtering deletions, and formatting the read data for display on display 410 or use by client device 408.

Client device 408 can be a thin client or thick client computing device. In various embodiments, client terminal 408 can have a web browser (e.g., INTERNET EXPLORER™, FIREFOX™, SAFARI™, etc) that can be used to communicate information to and/or control the operation of the pre-processing module 412, mapping module 414, breakpoint detection engine 418, copy number analyzer 420, evaluation engine 422, and post processing engine 424 using a browser to control their function. For example, the client terminal 408 can be used to configure the operating parameters (e.g., match scoring parameters, annotations parameters, filtering parameters, data security and retention parameters, etc.) of the various modules, depending on the requirements of the particular application. Similarly, client terminal 408 can also be configure to display the results of the analysis performed by the structural variant module 416 and the nucleic acid sequencer 404.

It should be understood that the various data stores disclosed as part of system 400 can represent hardware-based storage devices (e.g., hard drive, flash memory, RAM, ROM, network attached storage, etc.) or instantiations of a database stored on a standalone or networked computing device(s).

It should also be appreciated that the various data stores and modules/engines shown as being part of the system 400 can be combined or collapsed into a single module/engine/data store, depending on the requirements of the particular application or system architecture. Moreover, in various embodiments, the system 400 can comprise additional modules, engines, components or data stores as needed by the particular application or system architecture.

In various embodiments, the system 400 can be configured to process the nucleic acid reads in color space. In various embodiments, system 400 can be configured to process the nucleic acid reads in base space. In various embodiments, system 400 can be configured to process the nucleic acid sequence reads in flow space. It should be understood, however, that the system 400 disclosed herein can process or analyze nucleic acid sequence data in any schema or format as long as the schema or format can convey the base identity and position of the nucleic acid sequence.

Figure 5:
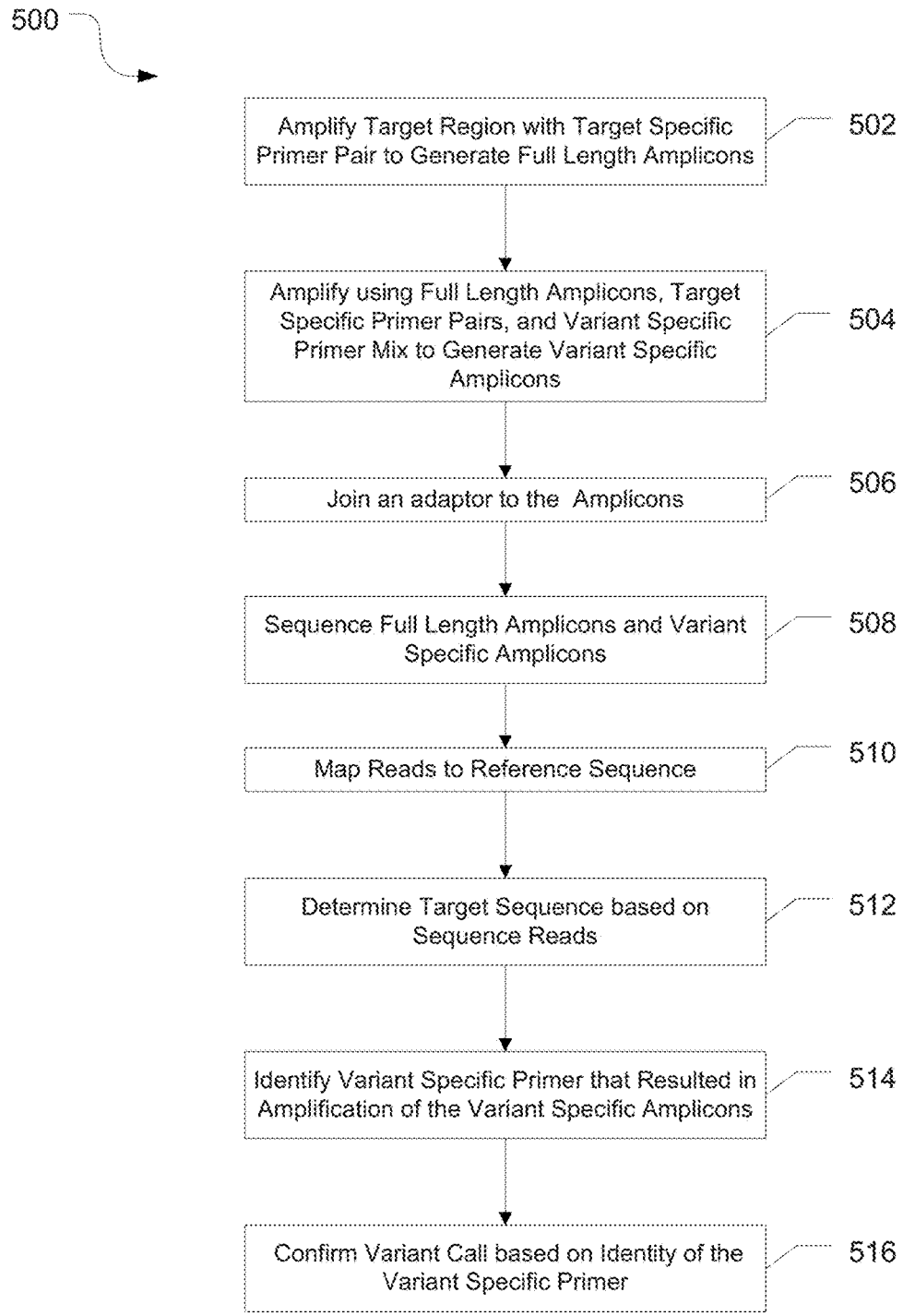
FIG. 5 is a flow diagram illustrating an exemplary method of validating sequencing results, in accordance with various embodiments.

FIG. 5 is a flow diagram illustrating an exemplary method 500 of identifying and verifying variants in a nucleic acid sample. At 502, a target region of the nucleic acid sample can be amplified using target specific primers to produce full length target amplicons. The target specific primers can flank the target region allowing amplification of the nucleic acid sequence between the target specific primers. In various embodiments, target specific primer pairs for multiple targets can be combined in a multiplex PCR reaction.

At 504, variant specific amplicons can be produced by the amplification of the target region using a combination of target specific primers and variant specific primers. The variant specific primers can include a variant specific barcode region and a variant sequence region. The variant specific barcode region can be used to uniquely identify the variant. Furthermore, the variant specific barcode regions can be assigned to provide a greater difference in the signal or series of signals detected by the sequencing instrument than the variant alone. For example, the variant specific primers can include a set of primers that cover a range of homopolymer lengths, such as a variant specific primer for each length between 6 and 12. In various embodiments, each variant specific primer can include a barcode region that contains a barcode sequence that corresponds to the length of the homopolymer in the same primer. In various embodiments, the variant sequence region can include left and right anchor regions corresponding to sequence on either side of the variant.

In various embodiments, the variant specific primers can be produced substantially simultaneously to the full length target amplicons, such as by combining the target specific primers and the variant specific primers in the PCR reaction mix. Generally, when combining to produce both full length target amplicons and variant specific amplicons in the same reaction, the amount of target specific primers should be in an excess relative to the variant specific primers to create a sufficient amount of full length target amplicons. Alternatively, sufficient full length target amplicons can be generated by amplification using target specific primers separate from the reaction to produce the variant specific amplicons, either by performing the different amplifications sequentially or at substantially the same time in different reaction vessels.

At 506, adaptor sequences can be joined to the amplicons. In various embodiments, the adaptor sequences can include sample specific barcode sequences. When sample specific barcode sequences are used, amplicons from multiple samples can be pooled and sequenced together, relying on the sample specific barcode sequences to differentiate the sequencing data during later analysis.

At 508, the full length target amplicons and the variant specific amplicons can be sequenced, and at 510, the sequencing reads can be mapped or aligned to a reference sequence.

At 512, the aligned reads of the full length target amplicons can be used to determine the sequence of the target region. Candidate variants can be identified where the sequences of the reads differ from the reference sequence. Additionally, the candidate variants can be scored based on various factors such as number of reads supporting the candidate variant, the difference in the fit of the sequencing data to the candidate variant versus the reference sequence, the probability the data supporting the candidate variant could be the result of a sequencing error, and the like.

At 514, variant specific amplicons corresponding to the position of the candidate variant can be identified. The variant specific amplicons can be shorter than the full length target amplicons and have a length corresponding to the distance between the position of the candidate variant and one of the target specific primers. Variant specific amplicons that correspond to the candidate variant can be identified based on an alignment of the variant specific amplicon to the region between the candidate variant and the target specific primer. Additionally, the variant specific barcode sequence of the variant specific amplicon can be determined, and the identity of the variant specific sequence can be determined based on the variant specific barcode sequence.

At 516, the candidate variant can be confirmed based on the presence of variant specific amplicons that correspond to the position of the candidate variant that include a variant specific sequence matching the candidate variant. For example, a candidate variant that includes a homopolymer 'A' of length 8 can be confirmed when variant specific amplicons containing the variant specific barcode corresponding to a homopolymer 'A' of length 8 is present and mapped to the location of the homopolymer 'A' of length 8. Alternatively, if the full length target amplicons fail to distinguish between a homopolymer of length 8 and a homopolymer of length 9, the presence of variant specific amplicons corresponding to the homopolymer of length 8 and the absence of variant specific amplicons corresponding to the homopolymer of length 9 can be used to confirm that the homopolymer length for the nucleic acid sample is 8 rather than 9.

In various embodiments, the sequence of clinically significant positions can be confirmed based on the presence and absence of corresponding variant specific amplicons. For example, when a drug is indicated for individuals with an 'A' at a particular genomic position and contraindicated for individuals without an 'A' at the position, variant specific primers corresponding to 'A', 'C', 'G', and 'T' and the position can be used. The presence of the 'A' variant specific amplicons could be used to verify sequencing results that indicate there is an 'A' at the position and that the individual may be a candidate for the drug. Alternatively, the presence of 'C', 'G', or 'T' variant specific amplicons and the absence of 'A' variant specific amplicons could be used to verify sequences results that indicate there is not an 'A' at the position and that the individual may not be a candidate for the drug.

In various embodiments, the methods of the present teachings may be implemented in a software program and applications written in conventional programming languages such as C, C++, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A method comprising:
amplifying a target region of a nucleic acid sample in the presence of a primer pool to produce a plurality of amplicons, the primer pool including a first and second target specific primers and a variant specific primer, the variant specific primer including a variant specific barcode sequence and a variant sequence;
sequencing the amplicons to generate a plurality of reads;
aligning the reads to a reference sequence; and
verifying the presence of a variant at a location based on identifying reads containing the variant specific barcode sequence that map to the location.

2. The method of claim 1, wherein the variant includes a homopolymer.

3. The method of claim 1, wherein the variant includes a single nucleotide polymorphism.

4. The method of claim 1, further comprising amplifying the target region of a nucleic acid sample in the presence of the first and second target specific primers to produce the full length target amplicons.

5. The method of claim 4, further comprising determining the sequence of the target region of the nucleic acid sample based on the sequence of the reads from the full length target amplicons.

6. The method of claim 1, further comprising joining an adaptor to amplicons prior to sequencing.

7. The method of claim 6, wherein the adaptor includes a sample specific barcode sequence.

8. The method of claim 7, further comprising identifying that a read corresponds to the nucleic acid sample based on the presence of the sample specific barcode sequence.

9. A method comprising:
amplifying a target region of a nucleic acid sample in the presence of first and second target specific primers to produce a plurality of full length target amplicons;
amplifying the target region of a nucleic acid sample in the presence of first and second target specific primers and a variant specific primer, the variant specific primer including a variant specific barcode sequence and a variant sequence, to produce a plurality of variant specific amplicons;
sequencing the full length target amplicons to generate a plurality of full length target reads;
sequencing the variant specific amplicons to generate a plurality of variant specific reads;
aligning the full length target reads and variant specific reads to a reference sequence;
determining a sequence of the target region based on the sequence of the full length target reads; and
verifying the presence of a variant at a location in the target region based on identifying reads containing the variant specific barcode sequence that map to the location.

10. The method of claim 9, wherein the variant includes a homopolymer.

11. The method of claim 9, wherein the variant includes a single nucleotide polymorphism.

12. The method of claim 9, wherein amplifying to produce full length target amplicons and amplifying to produce variant specific amplicons occurs in the same multiplex PCR reaction.

13. The method of claim 12, wherein there is an excess of the first and second target specific primers relative to the variant specific primer.

14. The method of claim 9, further comprising joining an adaptor to the full length target amplicons and variant specific amplicons prior to sequencing.

15. The method of claim 14, wherein the adaptor includes a sample specific barcode sequence.

16. The method of claim 15, further comprising identifying that a read corresponds to the nucleic acid sample based on the presence of the sample specific barcode sequence.

* * * * *

SEQUENCE LISTING

```
<160> NUMBER OF SEQ ID NOS: 3

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggtaaaaaa t                                                            11

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaaaaaaaa                                                              10

<210> SEQ ID NO 3
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 3
tttttttttt                                                              10
```